(12) United States Patent
Sakamoto et al.

(10) Patent No.: US 7,642,386 B2
(45) Date of Patent: Jan. 5, 2010

(54) METHOD FOR PRODUCING ALCOHOL

(75) Inventors: Toru Sakamoto, Wakayama (JP);
Masanori Namba, Wakayama (JP);
Nobuhiro Tatsumi, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 11/817,921

(22) PCT Filed: Mar. 7, 2006

(86) PCT No.: PCT/JP2006/304829
§ 371 (c)(1),
(2), (4) Date: Feb. 20, 2008

(87) PCT Pub. No.: WO2006/095889
PCT Pub. Date: Sep. 14, 2006

(65) Prior Publication Data
US 2009/0023962 A1    Jan. 22, 2009

(30) Foreign Application Priority Data
Mar. 8, 2005    (JP) .............................. 2005-063360

(51) Int. Cl.
*C07C 27/04*    (2006.01)
*C07C 29/16*    (2006.01)
*C07C 51/377*    (2006.01)
(52) U.S. Cl. .................... 568/864; 568/885; 554/160
(58) Field of Classification Search ............... 568/864, 568/885; 554/160
See application file for complete search history.

(56) References Cited

U.S. PATENT DOCUMENTS

| 2,094,127 A | 9/1937 | Lazier et al. |
| 2,109,844 A | 3/1938 | Lazier et al. |
| 2,241,417 A | 5/1941 | Normann et al. |
| 2,313,692 A * | 3/1943 | Winer ..................... 554/144 |
| 4,982,020 A * | 1/1991 | Carduck et al. ............. 568/864 |
| 5,364,986 A | 11/1994 | Demmering et al. |
| 5,475,160 A | 12/1995 | Singleton et al. |
| 2006/0205965 A1 | 9/2006 | Sakamoto et al. |
| 2007/0032686 A1 | 2/2007 | Sakamoto et al. |

FOREIGN PATENT DOCUMENTS

| DE | 1 668 219 | 3/1972 |
| JP | 63 39829 | 2/1988 |
| WO | 03 093208 | 11/2003 |
| WO | 2005 026091 | 3/2005 |

* cited by examiner

*Primary Examiner*—Sikarl A Witherspoon
(74) *Attorney, Agent, or Firm*—Oblon, Spivak, McClelland, Maier & Neustadt, L.L.P.

(57) ABSTRACT

The invention relates to a process for producing an alcohol from fats and oils, including:
  step 1 of reacting starting fats and oils with water to produce a reaction product containing a glycerin unit, and
  step 2 of subjecting the reaction product obtained in step 1 to a hydrogenation reaction in the presence of a catalyst in the coexistence of water in an amount of 0.5 mole or more relative to 1 mole of the glycerin unit contained in the reaction product.

20 Claims, No Drawings

METHOD FOR PRODUCING ALCOHOL

FIELD OF THE INVENTION

The present invention relates to a process for producing an alcohol from fats and oils.

BACKGROUND OF THE INVENTION

Conventionally, a process for producing fatty alcohols by catalytically hydrogenating fatty esters of methanol obtained by transesterification of glyceride with methanol is used in the industrial production of fatty alcohols. Alternatively, a method of catalytically hydrogenating wax esters obtained by esterification of fatty alcohols and fatty acids obtained by hydrolysis of glyceride, is also used. These two-stage processes are economically very favorable because valuable glycerin can be obtained with a high yield and high purity.

On one hand, the direct catalytic hydrogenation of glyceride enables an industrially important fatty alcohol product to be directly obtained from naturally occurring fats and oils, but is not so used in industrial production. This is because a side reaction wherein initially formed glycerin is hydrogenated on the surface of a catalyst occurs in the direct catalytic hydrogenation of glycerin, and thus glycerin cannot be obtained in a high yield, so the direct catalytic hydrogenation process cannot be economically favorable to the 2-stage process. This is one reason that the method of directly hydrogenating glyceride is not used on an industrial scale.

Methods of obtaining fatty alcohols by directly hydrogenating glyceride are described in for example U.S. Pat. Nos. 2,094,127, 2,109,844 and 2,241,417. DE-A 1668219 describes a method of hydrogenating glyceride obtained from fats and oils. U.S. Pat. Nos. 5,364,986 and 5,475,160 also describe methods of directly hydrogenating glyceride.

SUMMARY OF THE INVENTION

The present invention provides a process for producing an alcohol from fats and oils including:

step 1: a first step of reacting starting fats and oils with water to produce a reaction product having a glycerin unit, and step 2: a second step of subjecting the reaction product obtained in step 1 to a hydrogenation reaction in the presence of a catalyst in the coexistence of water in an amount of 0.5 mole or more relative to 1 mole of the glycerin unit contained in the reaction product.

DETAILED DESCRIPTION OF THE INVENTION

The methods described in U.S. Pat. Nos. 2,094,127, 2,109,844 and 2,241,417 are carried out at a reaction temperature of 200 to 400° C. at a hydrogen pressure of 100 to 300 bar to give fatty alcohols, but the desired reaction product glycerin is obtained in a small amount, and instead of glycerin, a large amount of propane, propanol or propylene glycol is obtained.

DE-A 1668219 describes a problem that a side reaction of forming propylene glycol, propanol or propane instead of the necessary glycerin cannot be regulated.

In the method described in U.S. Pat. No. 5,364,986 or U.S. Pat. No. 5,475,160, the direct hydrogenation of glyceride into fatty alcohols is conducted by using a copper-based catalyst under relatively mild reaction conditions. In this method, 1,2-propanediol is formed in a high yield, and the production of glycerin is not contemplated.

The present invention provides an economically very favorable process for producing an alcohol from fats and oils, wherein glycerin can be recovered in a high yield.

The process for producing an alcohol according to the present invention is economically very favorable and industrially advantageous because glycerin can be recovered in a high yield by suppressing the decomposition of glycerin.

[Step 1]

Step 1 in the present invention is a step of reacting starting fats and oils with water to produce a reaction product containing a glycerin unit.

The starting fats and oils used in step 1 are not particularly limited, and contain principally glyceride. The fats and oils may include not only triglyceride but also diglyceride, monoglyceride, fatty acid etc., and it is possible to use vegetable oils such as soybean oil, rapeseed oil, coconut oil, palm oil and palm kernel oil, animal oils such as tallow and fish oil, and synthetic fats and oils. The fats and oils may be used singly or as a mixture of two or more thereof. As the fats and oils, either those subjected to pretreatment such as a de-acid treatment or desulfurization treatment or those not subjected to pretreatment may be used.

The reaction product containing a glycerin unit obtained in step 1 also includes unreacted materials, and materials having the glycerin unit are triglyceride, diglyceride, monoglyceride, glycerin etc.

In step 1, the method of adding water is not particularly limited, and may be added in either a gaseous or liquid state. For example, mention is made of a method wherein water is previously mixed with the starting fats and oils and then subjected to reaction by heating, a method wherein water or vapor is added to the heated starting fats and oils and then subjected to reaction, and a method of feeding starting fats and oils and water simultaneously to a heated reactor. From the viewpoint of improving glycerin selectivity, the mole number of water added is preferably 0.5 or more, more preferably 1 or more, even more preferably 2 or more, even more preferably 3 or more, times as many as the mole number of glyceride and fatty acid in the starting fats and oils. From the viewpoint of energy consumption, the number of moles of water added is preferably 10,000 or less, more preferably 5,000 or less, even more preferably 1,000 or less, even more preferably 500 or less, times as many as the mole number of glyceride and fatty acid in the starting fats and oils. The reactor used in step 1 is not particularly limited and may be an ordinarily used apparatus. For example, a tubular reactor etc. can be used.

The reaction in step 1 may be carried out by a method of using either a catalytic reaction or catalyst-free reaction. In the case of a catalyst-free reaction, the reaction temperature is preferably 100 to 350° C., and more preferably 200 to 300° C.

In step 1, it is not necessary for the degree of conversion of the starting fats and oils reacting with water to be 100 mol %, and in consideration of glycerin selectivity, the degree of conversion is preferably 10 mol % or more, more preferably 40 mol % or more, even more preferably 70 mol % or more, even more preferably 90 mol % or more.

[Step 2]

Step 2 in the present invention is a step of hydrogenating the reaction product obtained in step 1, in the presence of a catalyst and in the coexistence of water. From the viewpoint of improving glycerin selectivity, the amount of coexistent water is 0.5 mole or more, more preferably 1 mole or more, even more preferably 2 moles or more, even more preferably 3 moles or more, relative to 1 mole of the glycerin unit contained in the reaction product obtained in step 1. From the viewpoint of energy consumption, the amount of coexistent water is preferably 10,000 moles or less, more preferably 5,000 moles or less, even more preferably 1,000 moles or less, and even more preferably 500 moles or less, relative to 1 mole of the glycerin unit.

The glycerin unit contained in the reaction product obtained in step 1 includes glycerin units derived not only from diglyceride, monoglyceride and glycerin obtained in the reaction in step 1, but also from unreacted triglyceride.

The method of allowing water to be coexistent is not particularly limited, and water may be coexistent in either a gaseous or liquid state. For example, there is a method of pre-mixing water or vapor with the reaction product obtained in step 1 outside of a reactor and feeding the mixture to the reactor, or a method of sending water not consumed in the reaction in step 1 to step 2. Water formed in the reaction in step 2 may be coexistent. The reaction wherein water is formed includes hydrogenation reaction, esterification reaction, dehydration reaction, condensation reaction, etc. The method of allowing water to be coexistent may be a method wherein fatty acids other than the fatty acid obtained in step 1 are added to the reactor, and water formed by hydrogenation reaction of the fatty acids is allowed to be coexistent. From the viewpoint of the amount of water formed by the reaction, the mole number of the fatty acids is preferably 0.5 to 10,000, more preferably 1 to 5,000, even more preferably 3 to 500, relative to 1 mole of the glycerin unit contained in the reaction product obtained in step 1.

The fats and oils added are not particularly limited, and it is possible to use fatty acids derived from vegetable oils such as soybean oil, rapeseed oil, coconut oil, palm oil and palm kernel oil and fatty acids derived from animal oils such as tallow and fish oil, and mixed fatty acids can also be used.

In step 2, the pressure in the catalytic hydrogenation reaction is preferably 1 to 50 MPa, more preferably 2 to 30 MPa. The temperature is preferably 120 to 300° C., more preferably 150 to 280° C.

The reactor used in step 2 is not particularly limited insofar as the catalytic hydrogenation reaction is feasible, and the reactor may be an ordinarily used device. Examples of the reactor include a fluidized bed reactor wherein catalytic hydrogenation reaction is carried out with a catalyst dispersed in fluid, a moving bed reactor wherein catalytic hydrogenation reaction is carried out with fluid supplied while the whole catalyst layer drops gradually due to gravitational force, a fixed-bed reactor wherein catalytic hydrogenation reaction is carried out by supplying a fluid into a catalyst charged and fixed in the reactor, a multi-tube fixed-bed reactor wherein the temperature of a catalyst layer can be isothermal, and a batch reactor wherein hydrogenation is carried out in a vessel charged with a catalyst, starting materials and water.

The catalyst used in step 2 may be a known hydrogenation catalyst used in alcohol production, and is not particularly limited. For example, Co-based catalysts such as Co/Zr, Co/Mo and Co/Cr, Cu-based catalysts such as Cu/Cr and Cu/Zn, and noble metal-based catalysts such as Re, Rh, Ru and platinum. Among these catalysts, the Ru- and Co-based catalysts are preferable, and especially Co-based catalysts, particularly Co/Zr catalyst, are more preferable.

The form of the catalyst is not particularly limited and can be suitably selected from the forms of powder, granules, tablets, noodles, film, monolith, etc., depending on the type of reactor. When a catalyst precursor is used, the catalyst is obtained by reducing it with a reducing substance. The reducing substance used here includes hydrogen, carbon monoxide, ammonia, hydrazine, formaldehyde and methanol, and these reducing substances may be used singly or as a mixture thereof and may be used in the presence of an inert gas such as nitrogen. When the catalyst precursor is to be reduced, either a gaseous phase reduction method or a liquid phase reduction method conducted in a hydrocarbon such as liquid paraffin or in a solvent such as dioxane, alcohol or ester may be used.

In the method of the present invention, the whole or a part of glycerin formed in step 1 may be separated and recovered before step 2. As the method of separating and recovering glycerin, a method which involves settling or centrifugation to separate it into an aqueous phase and an oil phase or another method which involves distillation can be used.

The alcohols obtained by the production process of the present invention are glycerin and fatty alcohols derived from fatty acids constituting the starting fats and oils, and together with the fatty alcohols, glycerin can be recovered in a high yield.

EXAMPLES

The present invention is described by reference to the Examples below. The Examples are provided for mere illustration of the present invention and not intended to limit the present invention.

In Examples 1 to 3 and Comparative Examples 1 to 2, palm kernel oil (saponification value 244.8 mg KOH/g; water content 0.05%; acid value 0.17 mg KOH/g) subjected to de-acid treatment was used as the starting fats and oils.

Example 1

Step 1: A tubular reactor (volume 0.003 m$^3$) set at a temperature of 290° C. was arranged before a fixed-bed reactor used in step 2, and in this tubular reactor, the starting fats and oils were reacted with water to give a reaction product. The starting fats and oils were fed at a flow rate of 60 cc/hr into the tubular reactor and water was fed at a flow rate of 50 moles to 1 mole of the starting fats and oils.

Step 2: A fixed-bed reactor having a tube of 25 mm in inner diameter charged with 300 cc commercial molded Co/Zr catalyst (G-67 manufactured by Sud-Chemie Catalysts Inc.) activated under the conditions of a hydrogen pressure of 5 MPa, a temperature of 250° C., and 0.5 hour was used. The reaction product obtained in step 1 was fed to the fixed-bed reactor and subjected to catalytic hydrogenation reaction under the conditions of a pressure of 19.8 MPa, a catalyst layer temperature of 230° C., and 75 moles of hydrogen relative to 1 mole of the starting fats and oils.

The product obtained in an outlet of the fixed-bed reactor was separated, by adding water, into an oil phase and an aqueous phase, and the degree of conversion of the starting fats and oils, the content of fatty alcohol in the oil phase and the selectivity for glycerin were analyzed by gas chromatography. The results are shown in Table 1. The degree of conversion of the starting fats and oils was defined by the following equation:

Degree (%) of conversion of the starting fats and oils=100−$TGt$ wherein $TGt$ is the amount (wt %) of triglyceride in the oil phase.

The selectivity for glycerin was defined as the ratio (wt %) of glycerin to the total organic materials in the aqueous phase detected by gas chromatography. The materials other than the fatty alcohol in the oil phase were mainly wax ester, monoglyceride, diglyceride and triglyceride, and the materials other than glycerin in the aqueous phase were mainly propylene glycol, n-propanol and iso-propanol.

Example 2

Using the same tubular reactor and fixed-bed reactor as in Example 1, steps 1 and 2 were carried out in the same manner as in Example 1 except that the catalyst layer temperature in step 2 was changed into 210° C. The degree of conversion of the starting fats and oils in an outlet of the fixed-bed reactor, the content of fatty alcohol in the oil phase and the selectivity for glycerin were analyzed in the same manner as in Example 1. The results are shown in Table 1.

Comparative Example 1

Using the same fixed-bed reactor as in Example 1, catalytic hydrogenation reaction was carried out by adding only the starting fats and oils at a rate of 120 cc/hr to the reactor under the conditions of a pressure of 19.8 MPa, a catalyst layer temperature of 230° C., and 75 moles of hydrogen relative to 1 mole of the starting fats and oils, wherein step 1 was not conducted and water was not fed. The degree of conversion of the starting fats and oils in an outlet of the fixed-bed reactor, the content of fatty alcohol in the oil phase and the selectivity for glycerin were analyzed in the same manner as in Example 1. The results are shown in Table 1.

TABLE 1

|  | Degree of conversion of starting fats and oils (%) | Content (wt %) of fatty alcohol in the oil phase | Selectivity for glycerin (%) |
|---|---|---|---|
| Example 1 | 97.0 | 44.8 | 48.3 |
| Example 2 | 96.4 | 31.5 | 80.9 |
| Comparative example 1 | 74.1 | 40.0 | 1.0 |

Example 3

Step 1: 180 g starting fats and oils and water in 20 moles to 1 mole of the starting fats and oils were introduced into a 500-ml autoclave with a rotating stirring system, and then heated to 250° C. and subjected to hydrolysis reaction for 2 hours in a nitrogen atmosphere at a stirring rate of 900 rpm.

After the conclusion of the reaction, the fluid in the autoclave was transferred to a separable flask with a rotating stirring system and a jacket set at 50° C., stirred for 1 hour under the condition of a stirring rate of 600 rpm, and then left for 24 hours thereby being separated into an oil phase and an aqueous phase.

Step 2: 13.0 g commercial Co/Zr catalyst activated in the same manner as in Example 1, 125.2 g of the oil recovered in step 1, and water (67.9 g) in 83.7 moles to the glyceride unit in the oil recovered in step 1, were introduced into a 500-ml autoclave with a rotating stirring system, and then heated to 230° C. and subjected to catalytic hydrogenation reaction for hours under the conditions of a total pressure of 24.5 MPa and a stirring rate of 900 rpm.

The sample obtained after the conclusion of the reaction was separated by adding water into an oil phase and an aqueous phase, and the oil phase was analyzed by gas chromatography to analyze the degree of conversion of the starting fats and oils and the content of fatty alcohol in the oil phase. The aqueous phase separated after the hydrolysis reaction in step 1, and the aqueous phase separated after the hydrogenation reaction in step 2, were analyzed by gas chromatography to analyze the recovery degree of glycerin. The results are shown in Table 2.

The degree of conversion of the starting fats and oils after step 2 was defined by the following equation:

$$\text{Degree (\%) of conversion of starting fats and oils} = (1 - [\text{glyceride}]_t / [\text{glyceride}]_0) \times 100$$

wherein $[\text{glyceride}]_t$ is the total of triglyceride, diglyceride and monoglyceride in the oil phase after the hydrogenation reaction for 5 hours, and $[\text{glyceride}]_0$ is the total of triglyceride, diglyceride and monoglyceride in the starting fats and oils.

The recovery of glycerin was defined by the following equation:

$$\text{Recovery (\%) of glycerin} = [\text{glycerin}]_t / [\text{glycerin}]_0 \times 100$$

wherein $[\text{glycerin}]_t$ is the total of glycerin contained in the aqueous phase separated after the hydrogenation reaction in step 1 and glycerin in the aqueous phase after the hydrogenation reaction for 5 hours in step 2, and $[\text{glycerin}]_0$ is the amount of glycerin formed stoichiometrically from the starting fats and oils.

TABLE 2

|  | Degree(%) of conversion of starting fats and oils after step 1 | Degree(%) of conversion of starting fats and oils after step 2 | Content (wt %) of fatty alcohol in the oil phase | Degree(%) of recovering glycerin |
|---|---|---|---|---|
| Example 3 | 90.4 | 96.4 | 31.6 | 90.8 |

Comparative Example 2

15 g commercial Co/Zr catalyst activated in the same manner as in Example 1, 150 g starting fats and oils, and water in 20 moles to 1 mole of the starting fats and oils, were introduced into a 500-ml autoclave with a rotating stirring system, and then heated to 230° C. and subjected to catalytic hydrogenation reaction for 5 hours under the conditions of a total pressure of 24.5 MPa and a stirring rate of 900 rpm.

The degree of conversion of the starting fats and oils after the conclusion of the reaction, the content of fatty alcohol in the oil phase and the recovery of glycerin were analyzed in the same manner as in Example 3. The results are shown in Table 3.

TABLE 3

|  | Degree(%) of conversion of starting fats and oils | Content(wt %) of fatty alcohol in the oil phase | Degree(%) of recovering glycerin |
|---|---|---|---|
| Comparative example 2 | 88.8 | 7.8 | 76.8 |

The invention claimed is:

1. A process for producing glycerin and a fatty alcohol from a fat or oil, comprising the following:
   (1) reacting a starting fat or oil with water to produce a reaction product having a glycerin unit, and
   (2) hydrogenating the reaction product obtained in (1) in the presence of a catalyst in the coexistence of water in an amount of 0.5 mole or more relative to 1 mole of the glycerin unit contained in the reaction product, thereby producing said glycerin and fatty alcohol.

2. The process for producing glycerin and a fatty alcohol according to claim 1, wherein the water allowed to be coexistent in (2) is water not having been consumed in the reaction in (1).

3. The process for producing glycerin and a fatty alcohol according to claim 1, wherein the water allowed to be coexistent in (2) is water formed by the reaction in (2).

4. The process for producing glycerin and a fatty alcohol according to claim 1, wherein the water allowed to be coexistent in (2) is water added in (2).

5. The process for producing glycerin and a fatty alcohol according to claim 1, wherein the whole or a part of glycerin formed in (1) is separated and recovered before (2).

6. The process for producing glycerin and a fatty alcohol according to claim 1, wherein the amount of water is 1 mole or more relative to 1 mole of the glycerin unit contained in the reaction product.

7. The process for producing glycerin and a fatty alcohol according to claim 1, wherein the amount of water is 2 mole or more relative to 1 mole of the glycerin unit contained in the reaction product.

8. The process for producing glycerin and a fatty alcohol according to claim 1, wherein the amount of water is 3 mole or more relative to 1 mole of the glycerin unit contained in the reaction product.

9. The process for producing glycerin and a fatty alcohol according to claim 1, wherein the degree of conversion of the starting fats and oils in (1) is at least 10 mol %.

10. The process for producing glycerin and a fatty alcohol according to claim 1, wherein the degree of conversion of the starting fats and oils in (1) is at least 40 mol %.

11. The process for producing glycerin and a fatty alcohol according to claim 1, wherein the degree of conversion of the starting fats and oils in (1) is at least 70 mol %.

12. The process for producing glycerin and a fatty alcohol according to claim 1, wherein the degree of conversion of the starting fats and oils in (1) is at least 90 mol %.

13. The process for producing glycerin and a fatty alcohol according to claim 1, wherein the reaction in (1) is a reaction carried out at a temperature of from 100 to 350° C.

14. The process for producing glycerin and a fatty alcohol according to claim 13, wherein the temperature is from 200 to 300° C.

15. The process for producing glycerin and a fatty alcohol according to claim 1, wherein the pressure in the hydrogenating of (2) is from 1 to 50 MPa.

16. The process for producing glycerin and a fatty alcohol according to claim 15, wherein the pressure is from 2 to 30 MPa.

17. The process for producing glycerin and a fatty alcohol according to claim 1, wherein the hydrogenating in (2) is carried out at a temperature of from 120 to 300° C.

18. The process for producing glycerin and a fatty alcohol according to claim 17, wherein the temperature is from 150 to 280° C.

19. The process for producing glycerin and a fatty alcohol according to claim 1, wherein the starting fat or oil is palm kernel oil.

20. The process for producing glycerin and a fatty alcohol according to claim 1, wherein (1) is carried out in a first reactor and at least part of the glycerin formed is recovered before (2), and (2) is carried out in a second reactor.

* * * * *